United States Patent [19]

Liu et al.

[11] 4,223,154

[45] Sep. 16, 1980

[54] PREPARATION OF 2-(3-ARYL-5-ISOXAZOL) BENZOYL HALIDE

[75] Inventors: Kou-Chang Liu, Creve Coeur; Robert K. Howe, Bridgeton, both of Mo.

[73] Assignee: Monsanto Company, St. Louis, Mo.

[21] Appl. No.: 19,049

[22] Filed: Mar. 9, 1979

[51] Int. Cl.² ............... C07D 261/08; A01N 9/22
[52] U.S. Cl. ............................ 548/248; 548/240
[58] Field of Search ............... 260/307 H; 548/248

[56] References Cited

U.S. PATENT DOCUMENTS

| | | | |
|---|---|---|---|
| 3,947,263 | 3/1976 | Brouwer et al. | 71/76 |
| 3,964,892 | 6/1976 | Brouwer et al. | 71/92 |
| 4,032,644 | 6/1977 | Nadelson | 424/272 |
| 4,135,910 | 1/1979 | Howe | 71/92 |
| 4,140,515 | 2/1979 | Howe | 71/88 |

FOREIGN PATENT DOCUMENTS 1494877  12/1977  United Kingdom ............... 260/307 H

*Primary Examiner*—Anton H. Sutto
*Attorney, Agent, or Firm*—Patricia A. Coburn; Donald W. Peterson

[57] ABSTRACT

2-(3-Aryl-5-isoxazol) benzoyl halide is prepared by treating 3'-(Aryl)-spiro[isobenzofuran-1(3H), 5'(4'H)-isoxazol]-3-one with a reactive halide and water.

7 Claims, No Drawings

PREPARATION OF 2-(3-ARYL-5-ISOXAZOL) BENZOYL HALIDE

This invention relates to the preparation of 2-(3-Aryl-5-isoxazol) benzoyl halide by treatment of 3'-(Aryl)-spiro[isobenzofuran-1-(3H),5'(4'H)-isoxazol]-3-one with a halide in the presence of water. More specifically, benzoyl halides of the formula

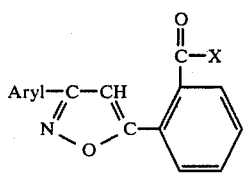

wherein X is a halogen, are prepared by treatment of a spiro compound of the formula

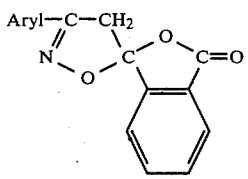

with reactive halides in the presence of a trace amount of water.

Reactive halides for the preparation of acid halides, especially acid chlorides, are well known in the art and include thionyl chloride, thionyl bromide, thionyl fluoride, phosphorus trichloride, phosphorus tribromide, oxalyl chloride, triphenyl phosphine-carbon tetrachloride, PCl$_5$, POBr$_3$, POCl$_3$ and the like. Specifically, reactive halides are those compounds containing halide ions that are known in the art to react with a carboxylic acid to form an acid halide.

The 3-(Aryl)-spiro[isobenzofuran-1(3H), 5'(4'H)-isoxazol]-3-one precursor has been disclosed in our co-pending application Ser. No. 971,462, filed Dec. 20, 1978, and is prepared as disclosed therein by reaction of a nitrile oxide with 3-methylenephthalide in accordance with the following equation:

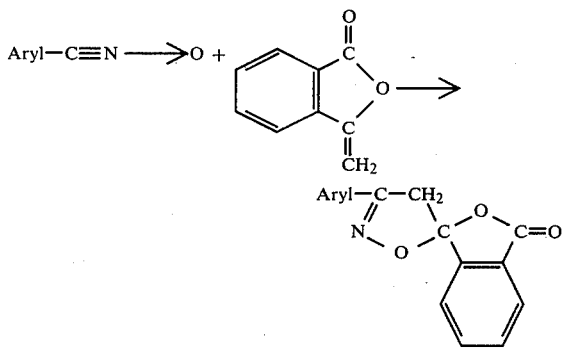

The benzoyl halide may be readily converted to 2-(3-Aryl-5-isoxazol) benzoates by an esterification reaction with appropriate esterification agents such as alcohols in a suitable solvent. Typical alcohols useful are methanol, ethanol, propanol, isopropanol, butyl alcohol and the like. Said 2-(3-Aryl-5-isoxazol) benzoates are useful as plant growth regulants and herbicides as taught by U.S. Patent Application Ser. No. 796,248, filed May 12, 1977, now abandoned, U.S. Patent Application Ser. No. 907,069, filed May 18, 1978 and U.S. Patent Application Ser. No. 966,403, filed Dec. 4, 1978, which are incorporated by reference.

To prepare the benzoyl halide, it is preferable to heat the spiro compound with the reactive halide at reflux. It is possible to utilize lower temperatures, as low as room temperature. However, their use will adversely effect the rate of reaction. The reaction readily proceeds at atmospheric pressure, although higher pressure could be utilized.

In accordance with the novel aspects of the present invention, it should be noted that the presence of a trace amount of water is required for reaction to proceed. If water were completely absent, the formation of the benzoyl halide would not occur. Typically, a few drops of water should be added to the reaction mixture. It is possible, however, that moisture in the atmosphere could provide sufficient water to drive the reaction. The critical factor is that a trace amount of water be provided from somewhere.

Since the Aryl radical takes no appreciable part in the chlorination reaction, any aromatic compound including heteroaryl may be used. Preferably, however, Aryl is a radical of the following formula

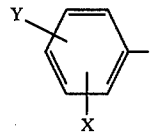

wherein X and Y are independently selected from the group consisting of hydrogen, halogen, lower alkyl, lower alkoxy, halo-lower-alkyl, phenoxy and phenyl.

As used herein, the terms "lower alkyl" and "lower alkoxy" are understood to include those alkyl and alkoxy groups having up to five carbon atoms, inclusive. Both straight as well as branched chain alkyl groups are contemplated.

The term "halo-lower-alkyl" as used herein is understood to mean those lower alkyl groups in which at least one and perhaps all of the hydrogen atoms have been replaced by halogen atoms. It is to be clearly understood that trifluoromethyl is contemplated as being a halo-lower-alkyl moiety.

The term "halogen" as used herein includes chlorine, bromine, fluorine and iodine.

By way of example and for purposes of illustration only, 2-[3-(3-trifluoromethylphenyl)-5-isoxazol]benzoyl chloride was prepared from a solution of 3'-(m-trifluoromethylphenyl)-spiro[isobenzofuran-1(3H), 5'(4'H)-isoxazol]-3-one (30 g., 0.90 mole), thionyl chloride (150 ml.) and water (5 drops) which was held at reflux for 2 hours, cooled and concentrated under vacuum to 32.7 g. of yellow solid, m.p. 86°–89° C. Recrystallization of 10 g. of the yellow solid from 50 ml. of carbon tetrachloride afforded 7.1 g. of a pale yellow solid, m.p. 90.5°–92° C. Recrystallization of 2.1 g. of the pale yellow solid once again from carbon tetrachloride gave 1.47 g. pure product as white crystals, m.p. 91°–92° C.

Anal. Calc'd. for C$_{17}$H$_9$F$_3$ClNO$_2$: C, 58.05; H, 2.58. Found: C, 57.67; H, 2.57.

The benzoyl chloride may be esterified as follows. 2-[3-[3-(trifluoromethyl)phenyl]-5-isoxazol] benzoyl chloride (5 g., 0.0162 mole) was added portionwise over 10 minutes to a stirred ice-cold solution of isopropanol (17 g., 0.202 mole) in 15 ml. of pyridine. The reaction mixture was allowed to stand at room temperature for one hour and then was taken up in 300 ml. of ether and washed three times with 1 Normal HCl, one time with sodium carbonate and finally with H$_2$O. The ether solution was dried and concentrated to yield 4.94g. of the isopropyl ester as a yellow oil. The oil was chromatographed on a silica gel column with 50% ethyl acetate-50% hexane as eluant to give a total of 3.7 g. of pure isopropyl ester, n$_D^{25}$=1.5426.

Anal. Calc'd. for C$_{20}$H$_{16}$F$_3$NO$_3$: C, 64.00; H, 4.30. Found: C, 63.99; H, 4.31.

The present invention, therefore, provides a rather fast, efficient manner for providing 2-(3-Aryl-5-isoxazol) benzoyl halide which can be esterified to provide 2-(3-Aryl-5-isoxazol) benzoates that are useful as herbicides and plant growth regulants.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for preparing 2-(3-Aryl-5-isoxazol) benzoyl halide having the formula

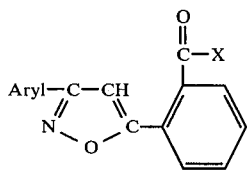

wherein X is a halogen which comprises treating 3'-(Aryl)-spiro[isobenzofuran-1(3H),5'(4'H)-isoxazol]-3-one having the formula

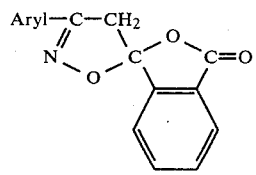

with a reactive halide and water.

2. A process according to claim 1 wherein said Aryl is

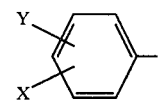

wherein X and Y are independently selected from the group consisting of hydrogen, halogen, lower alkyl, lower alkoxy, halo-lower-alkyl, phenoxy and phenyl.

3. A process according to claim 2 wherein X is hydrogen and Y is trifluoromethyl.

4. A process according to claim 1 wherein said reactive halide is selected from the group consisting of thionyl chloride, thionyl bromide, thionyl fluoride, phosphorus trichloride, phosphorus tribromide, oxalyl chloride, triphenyl phosphine-carbon tetrachloride, PCl$_5$, POBr$_3$ and POCl$_3$.

5. A process according to claim 4 wherein said reactive halide is selected from the group consisting of thionyl chloride, phosphorus trichloride, PCl$_5$ and POCl$_3$.

6. A process according to claim 1 wherein X is chlorine.

7. A process according to claim 5 wherein said reactive halide is thionyl chloride.

* * * * *